United States Patent [19]

Sprecher

[11] Patent Number: 5,578,705
[45] Date of Patent: Nov. 26, 1996

[54] CYTOPLASMIC ANTIPROTEINASE-2 CODING SEQUENCES

[75] Inventor: Cindy A. Sprecher, Seattle, Wash.

[73] Assignee: ZymoGenetics, Inc., Seattle, Wash.

[21] Appl. No.: 465,213

[22] Filed: Jun. 5, 1995

Related U.S. Application Data

[62] Division of Ser. No. 385,500, Feb. 8, 1995.

[51] Int. Cl.$^6$ .............................. C07K 14/00; C07K 1/00; C12N 15/00; C12N 15/09
[52] U.S. Cl. ...................... 530/388.26; 435/69.1; 435/240.2; 435/252.3; 435/320.1; 536/23.5; 530/350
[58] Field of Search ................. 435/69.1, 240.2, 435/252.3, 320.1; 536/23.5; 530/350, 388.26

[56] References Cited

PUBLICATIONS

Carrell et al., "The Serpins: Evolution and Adaptation in a Family of Protease Inhibitors", Cold Spring Harbor Symposia on Quantitative Biology, vol. LII, Cold Spring Harbor Laboratory, pp. 527–535 (1987).
Langer, "New Methods of Drug Delivery" *Science* 249:1527–1533 (Sep. 1990).
Deutscher, "Maintaining Protein Stability" *Meths. Enzymol.* 182:83–89 (1990).
Carrell et al., "Mobile Reactive Centre of Serpins and the Control of Thrombosis" *Nature* 353:576–578 (Oct. 1991).
Ray et al., "Viral Inhibition of Inflammation: Cowpox Virus Encodes and Inhibitor of the Interleukin–1β Converting Enzyme", *Cell* 69:597–604 (May, 1992).
Remold–O'Donnell et al., "Sequence and Molecular Characerization of Human Monocyte/Neutrophil Elastase Inhibitor", *Proc. Natl. Acad. Sci. USA*, 89:5635–5639 (Jun. 1992).
Lomas et al., "Inhibition of Plasmin, Urokinase, Tissue Plasminogen Activator, and $C_{1S}$ by a Myxoma Virus Serine Proteinase Inhibitor" *J. Biol. Chem.* 268:516–521 (Jan. 1993).
Remold –O'Donnell, "The Ovalbumin Family of Serpin Proteins" *FEBS* 315: 105–108 (Jan. 1993).
Coughlin et al., "Cloning and Molecular Characerization of a Human Intracellular Serine Proteinase Inhibitor", *Proc. Natl. Acad. Sci. USA* 90:9417–9421 (Oct. 1993).
Morgenstern et al., "Isolation and Characterization of an Intracellular Serine Proteinase Inhibitor from a Monkey Kidney Epithelia Cell Line", *J. Biol. Chem.* 268:21560–21568 (Oct. 1993).
Miura et al., "Induction of Apoptosis in Fibroblasts by IL–1β–Converting Enzyme, a Mammalian Homolog of the C. elegans Cell Death Gene ced–3", *Cell* 75:653–660 (Nov. 1993).
Yuan et al., "The C. elegans Cell Death Gene ced–3 Encodes a Protein Similar to Mammalian Interleukin–1β–Converting Enzyme" *Cell* 75:641–652 (Nov. 1993).
Gagliardini et al., "Prevention of Vertebrate Neuronal Death by the crmA Gene", *Science* 263: 826–828 (Feb. 1994).
Potempa et al., "The Serpin Superfamily of Proteinase Inhibitors: Structure, Function, and Regulation" *J. Biol. Chem.* 269: 15957–15960 (Jun. 1994).
Wang et al., "Ich–1, an Ice/ced–3–Related Gene, Encodes Both Positive and Negative Regulators of Programmed Cell Death", *Cell* 78: 739–750 (Sep. 1994).
Morgenstern et al., "Complementary DNA Cloning and Kinetic Characterization of a Novel Intracellular Serine Proteinase Inhibitor: Mechanism of Action with Trypsin and Factor Xa as Model Proteinase", *Biochem.* 33:3432–3441 (1994).
Patston et al., "A Database of Recombinant Wild–type and Mutant Serpins" *Thromb. Haemostas.* 72:166–179 (1994).

*Primary Examiner*—Mindy Fleisher
*Assistant Examiner*—Bonnie D. Weiss
*Attorney, Agent, or Firm*—Townsend and Townsend and Crew LLP

[57] ABSTRACT

Cytopasmic Antiproteinase-2 and Cytoplasmic Antiproteinase-3 nucleic acids and serine protease inhibitor proteins encoded thereby are useful in the purification of proteins and in the treatment of inflammatory diseases and diseases involving apoptosis.

3 Claims, No Drawings

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 1425 base pairs
( B ) TYPE: nucleic acid -continued (C) STRANDEDNESS: single
(D) TOPOLOGY: linear ( i i ) MOLECULE TYPE: cDNA ( i x ) FEATURE:
(A) NAME/KEY: CDS
(B) LOCATION: 92..1213
(D) OTHER INFORMATION: /product="CYTOPLASMIC ANTIPROTEINASE-2 PROTEIN"

( x i ) SEQUENCE DESCRIPTION: SEQ ID NO:1:

```
GAATTCGGAG CATCTACAAA GGAGGAATAG TCAAAGCAGC AGCGGCGGCG GCGGCGGCGG            60

CAGCAGCAGC AGCAGCAGGA GACCTTCTCT G ATG GAT GAC CTC TGT GAA GCA             112
                                  Met Asp Asp Leu Cys Glu Ala
                                   1               5

AAT GGC ACT TTT GCC ATC AGC TTA TTT AAA ATA TTG GGG GAA GAG GAC            160
Asn Gly Thr Phe Ala Ile Ser Leu Phe Lys Ile Leu Gly Glu Glu Asp
         10              15              20

AAC TCA AGA AAC GTA TTC TTC TCT CCC ATG AGC ATC TCC TCT GCC CTG            208
Asn Ser Arg Asn Val Phe Phe Ser Pro Met Ser Ile Ser Ser Ala Leu
     25              30              35

GCC ATG GTC TTC ATG GGG GCA AAG GGA AGC ACT GCA GCC CAG ATG TCC            256
Ala Met Val Phe Met Gly Ala Lys Gly Ser Thr Ala Ala Gln Met Ser
 40              45              50              55

CAG GCA CTT TGT TTA TAC AAA GAC GGA GAT ATT CAC CGA GGT TTC CAG            304
Gln Ala Leu Cys Leu Tyr Lys Asp Gly Asp Ile His Arg Gly Phe Gln
             60              65              70

TCA CTT CTC AGT GAA GTT AAC AGA ACT GGC ACT CAG TAC TTG CTT AGA            352
Ser Leu Leu Ser Glu Val Asn Arg Thr Gly Thr Gln Tyr Leu Leu Arg
         75              80              85

ACT GCC AAC AGA CTC TTT GGA GAA AAG ACG TGT GAT TTC CTT CCA GAC            400
Thr Ala Asn Arg Leu Phe Gly Glu Lys Thr Cys Asp Phe Leu Pro Asp
         90              95             100

TTT AAA GAA TAC TGT CAG AAG TTC TAT CAG GCA GAG CTG GAG GAG TTG            448
Phe Lys Glu Tyr Cys Gln Lys Phe Tyr Gln Ala Glu Leu Glu Glu Leu
105             110             115

TCC TTT GCT GAA GAC ACT GAA GAG TGC AGG AAG CAT ATA AAT GAC TGG            496
Ser Phe Ala Glu Asp Thr Glu Glu Cys Arg Lys His Ile Asn Asp Trp
120             125             130             135

GTG GCA GAG AAG ACT GAA GGT AAG ATT TCA GAG GTA CTG GAT GCT GGG            544
Val Ala Glu Lys Thr Glu Gly Lys Ile Ser Glu Val Leu Asp Ala Gly
             140             145             150

ACA GTC GAT CCC CTG ACA AAG CTA GTC CTT GTG AAT GCC ATT TAT TTC            592
Thr Val Asp Pro Leu Thr Lys Leu Val Leu Val Asn Ala Ile Tyr Phe
             155             160             165

AAG GGA AAG TGG AAT GAG CAA TTT GAC AGA AAG TAC ACA AGG GGA ATG            640
Lys Gly Lys Trp Asn Glu Gln Phe Asp Arg Lys Tyr Thr Arg Gly Met
             170             175             180

CTC TTT AAA ACC AAC GAG GAA AAA AAG ACA GTG CAG ATG ATG TTT AAG            688
Leu Phe Lys Thr Asn Glu Glu Lys Lys Thr Val Gln Met Met Phe Lys
         185             190             195

GAA GCT AAG TTT AAA ATG GGG TAT GCG GAT GAG GTA CAC ACC CAG GTC            736
Glu Ala Lys Phe Lys Met Gly Tyr Ala Asp Glu Val His Thr Gln Val
200             205             210             215

CTG GAG CTG CCC TAT GTG GAA GAG GAG CTG AGC ATG GTC ATT CTG CTT            784
Leu Glu Leu Pro Tyr Val Glu Glu Glu Leu Ser Met Val Ile Leu Leu
             220             225             230

CCC GAT GAC AAC ACG GAC CTC GCC GTG GTG GAA AAA GCA CTT ACA TAT            832
Pro Asp Asp Asn Thr Asp Leu Ala Val Val Glu Lys Ala Leu Thr Tyr
             235             240             245

GAG AAA TTC AAA GCC TGG ACA AAT TCA GAA AAG TTG ACA AAA AGT AAG            880
```

|         |         |         |         |         |         |         |         |         |         |         |         |         |         |         |         |      |
|---------|---------|---------|---------|---------|---------|---------|---------|---------|---------|---------|---------|---------|---------|---------|---------|------|
| Glu     | Lys     | Phe 250 | Lys     | Ala     | Trp     | Thr     | Asn 255 | Ser     | Glu     | Lys     | Leu     | Thr 260 | Lys     | Ser     | Lys     |      |
| GTT Val | CAA Gln 265 | GTT Val | TTC Phe | CTT Leu | CCC Pro | AGA Arg 270 | TTA Leu | AAG Lys | CTG Leu | GAG Glu | GAG Glu 275 | AGT Ser | TAT Tyr | GAC Asp | TTG Leu | 928  |
| GAG Glu 280 | CCT Pro | TTC Phe | CTT Leu | CGA Arg | AGA Arg 285 | TTA Leu | GGA Gly | ATG Met | ATC Ile | GAT Asp 290 | GCT Ala | TTT Phe | GAC Asp | GAA Glu | GCC Ala 295 | 976  |
| AAG Lys | GCA Ala | GAC Asp | TTT Phe | TCT Ser 300 | GGA Gly | ATG Met | TCA Ser | ACT Thr | GAG Glu 305 | AAG Lys | AAT Asn | GTG Val | CCT Pro | CTG Leu 310 | TCC Ser | 1024 |
| AAG Lys | GTT Val | GCC Ala | CAC His 315 | AAG Lys | TGC Cys | TTC Phe | GTG Val | GAG Glu 320 | GTC Val | AAT Asn | GAG Glu | GAA Glu | GGC Gly 325 | ACA Thr | GAG Glu | 1072 |
| GCT Ala | GCC Ala | GCA Ala 330 | GCC Ala | ACT Thr | GCT Ala | GTG Val 335 | GTC Val | AGG Arg | AAT Asn | TCC Ser | CGG Arg 340 | TGC Cys | AGC Ser | AGA Arg | ATG Met | 1120 |
| GAG Glu | CCA Pro 345 | AGA Arg | TTC Phe | TGT Cys | GCA Ala | GAC Asp 350 | CAC His | CCT Pro | TTT Phe | CTT Leu | TTC Phe 355 | TTC Phe | ATC Ile | AGG Arg | CGC Arg | 1168 |
| CAC His 360 | AAA Lys | ACC Thr | AAC Asn | TGC Cys | ATC Ile 365 | TTG Leu | TTC Phe | TGT Cys | GGC Gly | AGG Arg 370 | TTC Phe | TCT Ser | TCT Ser | CCG Pro |  | 1213 |

```
TAAAGAGGAG CAATTGCTGT ACATACCCTC CTTTCCTTCT ACCTATCTTG CCTTAATTAA    1273

CATTCCCTGT GACCTAGTTG GTGCAGTGGC TTGAATGCCA AAATAAAGCG TGTGCACTGG    1333

AAAAAAAAAA AAAAAAAAAA AAAAAAAAAA AAAAAAAAAA AAAAACCGA  ATTCCGCCGA    1393

TACTGACGGG CTCCAGGAGT CAATCACTAG TG                                  1425
```

( 2 ) INFORMATION FOR SEQ ID NO:2:

( i ) SEQUENCE CHARACTERISTICS:
        ( A ) LENGTH: 374 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|         |         |         |         |         |         |         |         |         |         |         |         |         |         |         |         |
|---------|---------|---------|---------|---------|---------|---------|---------|---------|---------|---------|---------|---------|---------|---------|---------|
| Met 1   | Asp     | Asp     | Leu     | Cys 5   | Glu     | Ala     | Asn     | Gly     | Thr 10  | Phe     | Ala     | Ile     | Ser     | Leu 15  | Phe     |
| Lys     | Ile     | Leu     | Gly 20  | Glu     | Glu     | Asp     | Asn     | Ser 25  | Arg     | Asn     | Val     | Phe     | Phe 30  | Ser     | Pro     |
| Met     | Ser     | Ile 35  | Ser     | Ser     | Ala     | Leu     | Ala 40  | Met     | Val     | Phe     | Met     | Gly 45  | Ala     | Lys     | Gly     |
| Ser     | Thr 50  | Ala     | Ala     | Gln     | Met     | Ser 55  | Gln     | Ala     | Leu     | Cys     | Leu 60  | Tyr     | Lys     | Asp     | Gly     |
| Asp 65  | Ile     | His     | Arg     | Gly     | Phe 70  | Gln     | Ser     | Leu     | Leu     | Ser 75  | Glu     | Val     | Asn     | Arg     | Thr 80  |
| Gly     | Thr     | Gln     | Tyr     | Leu 85  | Leu     | Arg     | Thr     | Ala     | Asn 90  | Arg     | Leu     | Phe     | Gly     | Glu 95  | Lys     |
| Thr     | Cys     | Asp     | Phe 100 | Leu     | Pro     | Asp     | Phe     | Lys 105 | Glu     | Tyr     | Cys     | Gln     | Lys 110 | Phe     | Tyr     |
| Gln     | Ala     | Glu     | Leu 115 | Glu     | Glu     | Leu     | Ser     | Phe 120 | Ala     | Glu     | Asp     | Thr     | Glu 125 | Glu     | Cys     |
| Arg     | Lys     | His 130 | Ile     | Asn     | Asp     | Trp     | Val 135 | Ala     | Glu     | Lys     | Thr     | Glu 140 | Gly     | Lys     | Ile     |
| Ser 145 | Glu     | Val     | Leu     | Asp     | Ala 150 | Gly     | Thr     | Val     | Asp     | Pro 155 | Leu     | Thr     | Lys     | Leu     | Val 160 |

| | | | | | | | | | | | | | | |
|---|---|---|---|---|---|---|---|---|---|---|---|---|---|---|
| Leu | Val | Asn | Ala | Ile | Tyr | Phe | Lys | Gly | Lys | Trp | Asn | Glu | Gln | Phe | Asp |
| | | | | 165 | | | | | 170 | | | | | 175 | |
| Arg | Lys | Tyr | Thr | Arg | Gly | Met | Leu | Phe | Lys | Thr | Asn | Glu | Glu | Lys | Lys |
| | | | 180 | | | | | 185 | | | | | 190 | | |
| Thr | Val | Gln | Met | Met | Phe | Lys | Glu | Ala | Lys | Phe | Lys | Met | Gly | Tyr | Ala |
| | | | 195 | | | | 200 | | | | | 205 | | | |
| Asp | Glu | Val | His | Thr | Gln | Val | Leu | Glu | Leu | Pro | Tyr | Val | Glu | Glu | Glu |
| | 210 | | | | | 215 | | | | | 220 | | | | |
| Leu | Ser | Met | Val | Ile | Leu | Leu | Pro | Asp | Asp | Asn | Thr | Asp | Leu | Ala | Val |
| 225 | | | | | 230 | | | | | 235 | | | | | 240 |
| Val | Glu | Lys | Ala | Leu | Thr | Tyr | Glu | Lys | Phe | Lys | Ala | Trp | Thr | Asn | Ser |
| | | | | 245 | | | | | 250 | | | | | 255 | |
| Glu | Lys | Leu | Thr | Lys | Ser | Lys | Val | Gln | Val | Phe | Leu | Pro | Arg | Leu | Lys |
| | | | 260 | | | | | 265 | | | | | 270 | | |
| Leu | Glu | Glu | Ser | Tyr | Asp | Leu | Glu | Pro | Phe | Leu | Arg | Arg | Leu | Gly | Met |
| | | | 275 | | | | 280 | | | | | 285 | | | |
| Ile | Asp | Ala | Phe | Asp | Glu | Ala | Lys | Ala | Asp | Phe | Ser | Gly | Met | Ser | Thr |
| | 290 | | | | | 295 | | | | | 300 | | | | |
| Glu | Lys | Asn | Val | Pro | Leu | Ser | Lys | Val | Ala | His | Lys | Cys | Phe | Val | Glu |
| 305 | | | | | 310 | | | | | 315 | | | | | 320 |
| Val | Asn | Glu | Glu | Gly | Thr | Glu | Ala | Ala | Ala | Thr | Ala | Val | Val | Arg | |
| | | | | 325 | | | | | 330 | | | | | 335 | |
| Asn | Ser | Arg | Cys | Ser | Arg | Met | Glu | Pro | Arg | Phe | Cys | Ala | Asp | His | Pro |
| | | | 340 | | | | | 345 | | | | | 350 | | |
| Phe | Leu | Phe | Phe | Ile | Arg | Arg | His | Lys | Thr | Asn | Cys | Ile | Leu | Phe | Cys |
| | | | 355 | | | | | 360 | | | | | 365 | | |
| Gly | Arg | Phe | Ser | Ser | Pro | | | | | | | | | | |
| | | | 370 | | | | | | | | | | | | |

( 2 ) INFORMATION FOR SEQ ID NO:3:

( i ) SEQUENCE CHARACTERISTICS:
        ( A ) LENGTH: 1393 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 112..1239
        ( D ) OTHER INFORMATION: /product="CYTOPLASMIC ANTIPROTEINASE-3 PROTEIN"

( x i ) SEQUENCE DESCRIPTION: SEQ ID NO:3:

```
GAATTCGGCG CAGCAGCAGG GCCGGGTCCT GCGCCTCGGG GGTCGGCGTC CAGGCTCGGA        60

GCGCGGCACG GAGACGGCGG CAGCGCTGGA CTAGGTGGCA GGCCCTGCAT C ATG GAA        117
                                                        Met Glu
                                                         1
```

| ACT | CTT | TCT | AAT | GCA | AGT | GGT | ACT | TTT | GCC | ATA | CGC | CTT | TTA | AAG | ATA | 165 |
|---|---|---|---|---|---|---|---|---|---|---|---|---|---|---|---|---|
| Thr | Leu | Ser | Asn | Ala | Ser | Gly | Thr | Phe | Ala | Ile | Arg | Leu | Leu | Lys | Ile | |
| | | 5 | | | | | 10 | | | | | 15 | | | | |

| CTG | TGT | CAA | GAT | AAC | CCT | TCG | CAC | AAC | GTG | TTC | TGT | TCT | CCT | GTG | AGC | 213 |
|---|---|---|---|---|---|---|---|---|---|---|---|---|---|---|---|---|
| Leu | Cys | Gln | Asp | Asn | Pro | Ser | His | Asn | Val | Phe | Cys | Ser | Pro | Val | Ser | |
| | 20 | | | | | 25 | | | | | 30 | | | | | |

| ATC | TCC | TCT | GCC | CTG | GCC | ATG | GTT | CTC | CTA | GGG | GCA | AAG | GGA | AAC | ACC | 261 |
|---|---|---|---|---|---|---|---|---|---|---|---|---|---|---|---|---|
| Ile | Ser | Ser | Ala | Leu | Ala | Met | Val | Leu | Leu | Gly | Ala | Lys | Gly | Asn | Thr | |
| 35 | | | | | 40 | | | | | 45 | | | | | 50 | |

-continued

| | | | | | | | | | | | | | | | | |
|---|---|---|---|---|---|---|---|---|---|---|---|---|---|---|---|---|
| GCA | ACC | CAG | ATG | GCC | CAG | GCA | CTG | TCT | TTA | AAC | ACA | GAG | GAA | GAC | ATT | 309 |
| Ala | Thr | Gln | Met | Ala | Gln | Ala | Leu | Ser | Leu | Asn | Thr | Glu | Glu | Asp | Ile | |
| | | | 55 | | | | | 60 | | | | | | 65 | | |
| CAT | CGG | GCT | TTC | CAG | TCG | CTT | CTC | ACT | GAA | GTG | AAC | AAG | GCT | GGC | ACA | 357 |
| His | Arg | Ala | Phe | Gln | Ser | Leu | Leu | Thr | Glu | Val | Asn | Lys | Ala | Gly | Thr | |
| | | | 70 | | | | | 75 | | | | | 80 | | | |
| CAG | TAC | CTG | CTG | AGA | ACG | GCC | AAC | AGG | CTC | TTT | GGA | GAG | AAA | ACT | TGT | 405 |
| Gln | Tyr | Leu | Leu | Arg | Thr | Ala | Asn | Arg | Leu | Phe | Gly | Glu | Lys | Thr | Cys | |
| | | | 85 | | | | | 90 | | | | | 95 | | | |
| CAG | TTC | CTC | TCA | ACG | TTT | AAG | GAA | TCC | TGT | CTT | CAA | TTC | TAC | CAT | GCT | 453 |
| Gln | Phe | Leu | Ser | Thr | Phe | Lys | Glu | Ser | Cys | Leu | Gln | Phe | Tyr | His | Ala | |
| | | | 100 | | | | | 105 | | | | | 110 | | | |
| GAG | CTG | AAG | GAG | CTT | TCC | TTT | ATC | AGA | GCT | GCA | GAA | GAG | TCC | AGG | AAA | 501 |
| Glu | Leu | Lys | Glu | Leu | Ser | Phe | Ile | Arg | Ala | Ala | Glu | Glu | Ser | Arg | Lys | |
| 115 | | | | | 120 | | | | | 125 | | | | | 130 | |
| CAC | ATC | AAC | ACC | TGG | GTC | TCA | AAA | AAG | ACC | GAA | GGT | AAA | ATT | GAA | GAG | 549 |
| His | Ile | Asn | Thr | Trp | Val | Ser | Lys | Lys | Thr | Glu | Gly | Lys | Ile | Glu | Glu | |
| | | | | 135 | | | | | 140 | | | | | 145 | | |
| TTG | TTG | CCG | GGT | AGC | TCA | ATT | GAT | GCA | GAA | ACC | AGG | CTG | GTT | CTT | GTC | 597 |
| Leu | Leu | Pro | Gly | Ser | Ser | Ile | Asp | Ala | Glu | Thr | Arg | Leu | Val | Leu | Val | |
| | | | 150 | | | | | 155 | | | | | 160 | | | |
| AAT | GCC | ATC | TAC | TTC | AAA | GGA | AAG | TGG | AAT | GAA | CCG | TTT | GAC | GAA | ACA | 645 |
| Asn | Ala | Ile | Tyr | Phe | Lys | Gly | Lys | Trp | Asn | Glu | Pro | Phe | Asp | Glu | Thr | |
| | | 165 | | | | | 170 | | | | | 175 | | | | |
| TAC | ACA | AGG | GAA | ATG | CCC | TTT | AAA | ATA | AAC | CAG | GAG | GAG | CAA | AGG | CCA | 693 |
| Tyr | Thr | Arg | Glu | Met | Pro | Phe | Lys | Ile | Asn | Gln | Glu | Glu | Gln | Arg | Pro | |
| | 180 | | | | | 185 | | | | | 190 | | | | | |
| GTG | CAG | ATG | ATG | TAT | CAG | GAG | GCC | ACG | TTT | AAG | CTC | GCC | CAC | GTG | GGC | 741 |
| Val | Gln | Met | Met | Tyr | Gln | Glu | Ala | Thr | Phe | Lys | Leu | Ala | His | Val | Gly | |
| 195 | | | | | 200 | | | | | 205 | | | | | 210 | |
| GAG | GTG | CGC | GCG | CAG | CTG | CTG | GAG | CTG | CCC | TAC | GCC | AGG | AAG | GAG | CTG | 789 |
| Glu | Val | Arg | Ala | Gln | Leu | Leu | Glu | Leu | Pro | Tyr | Ala | Arg | Lys | Glu | Leu | |
| | | | | 215 | | | | | 220 | | | | | 225 | | |
| AGC | CTG | CTG | GTG | CTG | CTG | CCT | GAC | GAC | GGC | GTG | GAG | CTC | AGC | ACG | GTG | 837 |
| Ser | Leu | Leu | Val | Leu | Leu | Pro | Asp | Asp | Gly | Val | Glu | Leu | Ser | Thr | Val | |
| | | | 230 | | | | | 235 | | | | | 240 | | | |
| GAA | AAA | AGT | CTC | ACT | TTT | GAG | AAA | CTC | ACA | GCC | TGG | ACC | AAG | CCA | GAC | 885 |
| Glu | Lys | Ser | Leu | Thr | Phe | Glu | Lys | Leu | Thr | Ala | Trp | Thr | Lys | Pro | Asp | |
| | | 245 | | | | | 250 | | | | | 255 | | | | |
| TGT | ATG | AAG | AGT | ACT | GAG | GTT | GAA | GTT | CTC | CTT | CCA | AAA | TTT | AAA | CTA | 933 |
| Cys | Met | Lys | Ser | Thr | Glu | Val | Glu | Val | Leu | Leu | Pro | Lys | Phe | Lys | Leu | |
| | 260 | | | | | 265 | | | | | 270 | | | | | |
| CAA | GAG | GAT | TAT | GAC | ATG | GAA | TCT | GTG | CTT | CGG | CAT | TTG | GGA | ATT | GTT | 981 |
| Gln | Glu | Asp | Tyr | Asp | Met | Glu | Ser | Val | Leu | Arg | His | Leu | Gly | Ile | Val | |
| 275 | | | | | 280 | | | | | 285 | | | | | 290 | |
| GAT | GCC | TTC | CAA | CAG | GGC | AAG | GCT | GAC | TTG | TCG | GCA | ATG | TCA | GCG | GAG | 1029 |
| Asp | Ala | Phe | Gln | Gln | Gly | Lys | Ala | Asp | Leu | Ser | Ala | Met | Ser | Ala | Glu | |
| | | | | 295 | | | | | 300 | | | | | 305 | | |
| AGA | GAC | CTG | TGT | CTG | TCC | AAG | TTC | GTG | CAC | AAG | AGT | TTT | GTG | GAG | GTG | 1077 |
| Arg | Asp | Leu | Cys | Leu | Ser | Lys | Phe | Val | His | Lys | Ser | Phe | Val | Glu | Val | |
| | | | 310 | | | | | 315 | | | | | 320 | | | |
| AAT | GAA | GAA | GGC | ACC | GAG | GCA | GCG | GCA | GCG | TCG | AGC | TGC | TTT | GTA | GTT | 1125 |
| Asn | Glu | Glu | Gly | Thr | Glu | Ala | Ala | Ala | Ala | Ser | Ser | Cys | Phe | Val | Val | |
| | | 325 | | | | | 330 | | | | | 335 | | | | |
| GCA | GAG | TGC | TGC | ATG | GAA | TCT | GGC | CCC | AGG | TTC | TGT | GCT | GAC | CAC | CCT | 1173 |
| Ala | Glu | Cys | Cys | Met | Glu | Ser | Gly | Pro | Arg | Phe | Cys | Ala | Asp | His | Pro | |
| | 340 | | | | | 345 | | | | | 350 | | | | | |
| TTC | CTT | TTC | TTC | ATC | AGG | CAC | AAC | AGA | GCC | AAC | AGC | ATT | CTG | TTC | TGT | 1221 |
| Phe | Leu | Phe | Phe | Ile | Arg | His | Asn | Arg | Ala | Asn | Ser | Ile | Leu | Phe | Cys | |
| 355 | | | | | 360 | | | | | 365 | | | | | 370 | |

```
GGC AGG TTC TCA TCG CCA TAAAGGGTGC ACTTACCGTG CACTCGGCCA                    1269
Gly Arg Phe Ser Ser Pro
            375

TTTCCCTCTT CCTGTGTCCC CAGATCCCCA CTACAGCTCC AAGAGGATGG GCCTAGAAAG          1329

CCAAGTGCAA AGATGAGGGC AGATTCTTTA CCTGTCTGCC CTCATGATTT GCCAGCATGA          1389

ATTC                                                                        1393
```

( 2 ) INFORMATION FOR SEQ ID NO:4:

( i ) SEQUENCE CHARACTERISTICS:
        ( A ) LENGTH: 376 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Glu Thr Leu Ser Asn Ala Ser Gly Thr Phe Ala Ile Arg Leu Leu
 1               5                  10                  15

Lys Ile Leu Cys Gln Asp Asn Pro Ser His Asn Val Phe Cys Ser Pro
             20                  25                  30

Val Ser Ile Ser Ser Ala Leu Ala Met Val Leu Leu Gly Ala Lys Gly
         35                  40                  45

Asn Thr Ala Thr Gln Met Ala Gln Ala Leu Ser Leu Asn Thr Glu Glu
     50                  55                  60

Asp Ile His Arg Ala Phe Gln Ser Leu Leu Thr Glu Val Asn Lys Ala
 65                  70                  75                  80

Gly Thr Gln Tyr Leu Leu Arg Thr Ala Asn Arg Leu Phe Gly Glu Lys
                 85                  90                  95

Thr Cys Gln Phe Leu Ser Thr Phe Lys Glu Ser Cys Leu Gln Phe Tyr
                100                 105                 110

His Ala Glu Leu Lys Glu Leu Ser Phe Ile Arg Ala Ala Glu Glu Ser
             115                 120                 125

Arg Lys His Ile Asn Thr Trp Val Ser Lys Lys Thr Glu Gly Lys Ile
130                 135                 140

Glu Glu Leu Leu Pro Gly Ser Ser Ile Asp Ala Glu Thr Arg Leu Val
145                 150                 155                 160

Leu Val Asn Ala Ile Tyr Phe Lys Gly Lys Trp Asn Glu Pro Phe Asp
                165                 170                 175

Glu Thr Tyr Thr Arg Glu Met Pro Phe Lys Ile Asn Gln Glu Glu Gln
                180                 185                 190

Arg Pro Val Gln Met Met Tyr Gln Glu Ala Thr Phe Lys Leu Ala His
        195                 200                 205

Val Gly Glu Val Arg Ala Gln Leu Leu Glu Leu Pro Tyr Ala Arg Lys
    210                 215                 220

Glu Leu Ser Leu Leu Val Leu Leu Pro Asp Asp Gly Val Glu Leu Ser
225                 230                 235                 240

Thr Val Glu Lys Ser Leu Thr Phe Glu Lys Leu Thr Ala Trp Thr Lys
                245                 250                 255

Pro Asp Cys Met Lys Ser Thr Glu Val Glu Val Leu Leu Pro Lys Phe
            260                 265                 270

Lys Leu Gln Glu Asp Tyr Asp Met Glu Ser Val Leu Arg His Leu Gly
        275                 280                 285

Ile Val Asp Ala Phe Gln Gln Gly Lys Ala Asp Leu Ser Ala Met Ser
    290                 295                 300

Ala Glu Arg Asp Leu Cys Leu Ser Lys Phe Val His Lys Ser Phe Val
```

```
305                         310                          315                         320
Glu Val Asn Glu Glu Gly Thr Glu Ala Ala Ala Ala Ser Ser Cys Phe
                325                      330                     335

Val Val Ala Glu Cys Cys Met Glu Ser Gly Pro Arg Phe Cys Ala Asp
            340                 345                 350

His Pro Phe Leu Phe Phe Ile Arg His Asn Arg Ala Asn Ser Ile Leu
        355                 360                 365

Phe Cys Gly Arg Phe Ser Ser Pro
    370             375
```

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (primer)

( i x ) FEATURE:
        ( A ) NAME/KEY: misc_feature
        ( B ) LOCATION: 1..21
        ( D ) OTHER INFORMATION: /standard_name="ZC6657"

( x i ) SEQUENCE DESCRIPTION: SEQ ID NO:5:

```
GCGGAATTCG AATCACAGGT T                                           21
```

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (primer)

( i x ) FEATURE:
        ( A ) NAME/KEY: misc_feature
        ( B ) LOCATION: 1..20
        ( D ) OTHER INFORMATION: /standard_name="ZC6658"

( x i ) SEQUENCE DESCRIPTION: SEQ ID NO:6:

```
ATAGAATTCA TCGCATTTCC                                             20
```

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (primer)

( i x ) FEATURE:
        ( A ) NAME/KEY: misc_feature
        ( B ) LOCATION: 1..24
        ( D ) OTHER INFORMATION: /standard_name="ZC6770"

( x i ) SEQUENCE DESCRIPTION: SEQ ID NO:7:

```
TCTCTTCTCA CCGAAGTGAA CAAG                                        24
```

( 2 ) INFORMATION FOR SEQ ID NO:8:

( i ) SEQUENCE CHARACTERISTICS:
        ( A ) LENGTH: 24 base pairs
        ( B ) TYPE: nucleic acid ( C ) STRANDEDNESS: single
         ( D ) TOPOLOGY: linear ( i i ) MOLECULE TYPE: DNA (primer)

( i x ) FEATURE:
         ( A ) NAME/KEY: misc_feature
         ( B ) LOCATION: 1..24
         ( D ) OTHER INFORMATION: /standard_name="ZC6771"

( x i ) SEQUENCE DESCRIPTION: SEQ ID NO:8:

TTCTGTCTTT TCAGCTACCC AGGT 24

( 2 ) INFORMATION FOR SEQ ID NO:9:

( i ) SEQUENCE CHARACTERISTICS:
         ( A ) LENGTH: 15 base pairs
         ( B ) TYPE: nucleic acid
         ( C ) STRANDEDNESS: single
         ( D ) TOPOLOGY: linear ( i i ) MOLECULE TYPE: DNA (primer)

( i x ) FEATURE:
         ( A ) NAME/KEY: misc_feature
         ( B ) LOCATION: 1..15
         ( D ) OTHER INFORMATION: /standard_name="ZC2682"

( x i ) SEQUENCE DESCRIPTION: SEQ ID NO:9:

GGTAGCGACC GGCGC 15

( 2 ) INFORMATION FOR SEQ ID NO:10:

( i ) SEQUENCE CHARACTERISTICS:
         ( A ) LENGTH: 15 base pairs
         ( B ) TYPE: nucleic acid
         ( C ) STRANDEDNESS: single
         ( D ) TOPOLOGY: linear ( i i ) MOLECULE TYPE: DNA (primer)

( i x ) FEATURE:
         ( A ) NAME/KEY: misc_feature
         ( B ) LOCATION: 1..15
         ( D ) OTHER INFORMATION: /standard_name="ZC2683"

( x i ) SEQUENCE DESCRIPTION: SEQ ID NO:10:

GACTCCTGGA GCCCG 15

( 2 ) INFORMATION FOR SEQ ID NO:11:

( i ) SEQUENCE CHARACTERISTICS:
         ( A ) LENGTH: 39 base pairs
         ( B ) TYPE: nucleic acid
         ( C ) STRANDEDNESS: single
         ( D ) TOPOLOGY: linear ( i i ) MOLECULE TYPE: DNA (primer)

( x i ) SEQUENCE DESCRIPTION: SEQ ID NO:11:

CTCCATTCTG CTGCACCGGG AATTCCTGAC CACAGCAGT 39

( 2 ) INFORMATION FOR SEQ ID NO:12:

( i ) SEQUENCE CHARACTERISTICS:
         ( A ) LENGTH: 39 base pairs
         ( B ) TYPE: nucleic acid
         ( C ) STRANDEDNESS: single
         ( D ) TOPOLOGY: linear ( i i ) MOLECULE TYPE: DNA (primer)

( x i ) SEQUENCE DESCRIPTION: SEQ ID NO:12:

AGATTCCATG CAGCACTCTG CAACTACAAA GCAGCTCGA 39

( 2 ) INFORMATION FOR SEQ ID NO:13:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

AATTAGGGAG ACCGGAATTC TGTGCTCTGT CAA 33

( 2 ) INFORMATION FOR SEQ ID NO:14:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

AATTTTGACA GAGCACAGAA TTCCGGTCTC CTT 33

( 2 ) INFORMATION FOR SEQ ID NO:15:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

AATTGAGCTC G 11

( 2 ) INFORMATION FOR SEQ ID NO:16:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

AATTCGAGCT C 11

CYTOPLASMIC ANTIPROTEINASE-2 CODING SEQUENCES

This application is a divisional of Ser. No. 08/385,500, filed Feb. 8, 1995, (pending) which is incorporated herein by reference.

BACKGROUND OF THE INVENTION

Serine proteases play a critical role in many physiological processes. For example, serine proteases are involved in blood coagulation, fibrinolysis, complement activation, and inflammation. The catalytic activity of these serine proteases is often regulated by members of a super-family of serine protease inhibitors called serpins. Serpins act to regulate the activity of serine proteases by binding stoichiometrically to the active sites of serine proteases and thus inactivating the enzymes. See Carrell, et al. (1987) *Cold Spring Harbor Symposia*, vol. LII, pp. 527–535 for a description of the general structural characteristics of serpins.

Many serpins are extracellular proteins which regulate extracellular processes such as blood coagulation, fibrinolysis and complement activation. In addition, there is a family of serpins structurally related to ovalbumin which lack secretory peptide sequences and which may function, in part, intracellularly. Several of this latter group of serpins are believed to play an important role in regulating serine protease activity in inflammation. Elastase inhibitor is an example of such a serpin which functions to regulate the activity of neutrophil elastase. Neutrophil elastase is stored in the azurophil granules of neutrophils, monocytes and macrophages, and degrades both phagocytized and extracellular substrates. Regulation of neutrophil elastase is important both in host defense mechanisms and also in the pathology of diseases such as arthritic joint diseases.

Interleukin-1β converting enzyme (ICE) is an another example of a cysteine protease that plays an important role in inflammation. ICE is responsible for the activation of interleukin-1β, which is a critical cytokine in the inflammatory process. Serpins which inhibit ICE may therefore play an important role in inflammation. One such serpin is a viral protein encoded by the cowpox virus crmA gene. It is believed that expression of crmA protein inhibits ICE and thereby blocks migration of inflammatory cells in cowpox lesions. (See Ray, C. A., et. al. (1992) Cell 69:597–604.) Isolated cellular serpins that inhibit ICE in a similar manner to the crmA protein can be useful in the modulation of the inflammatory response. Agents that modulate the inflammatory response can be used in the treatment of a variety of inflammatory diseases, such as rheumatoid arthritis.

ICE is but one member of a family of serine proteases that play important roles in normal physiology and in pathophysiology. For example, another member of the ICE family, Ich-1, is involved in regulation of apoptosis. Furthermore, evidence is accumulating that regulation of apoptosis plays a role in a variety of different diseases, including cancer. Therefore, isolated serpin molecules which inhibit Ich-1 could be used to regulate apoptosis and treat a number of diseases.

Isolated serpin molecules are also useful in the purification of a variety of proteins for use in medicine and industry. Protein degradation during purification by endogenous serine proteases is a common problem. Isolation of serpins inhibiting different serine proteases is useful to improve the purification of many different proteins. These and other needs are addressed by the present invention.

SUMMARY OF THE INVENTION

The present invention provides isolated nucleic acid molecules encoding mammalian CAP-2 and CAP-3 protein. The CAP-2 and CAP-3 proteins of the invention are homologous to the amino acid sequence depicted in SEQ ID NO:2 and SEQ ID NO:4, respectively, including the amino acid sequence depicted in SEQ ID NO:2 or SEQ ID NO:4, or an allelic variant thereof. Typically the CAP-2 or CAP-3 protein and polypeptides thereof will be capable of inhibiting serine protease activity. The isolated nucleic acid molecule, e.g., DNA or RNA, may encode human CAP-2 or CAP-3 protein.

Thus, in another aspect the invention includes isolated mammalian CAP-2 protein which is homologous to the amino acid sequence depicted in SEQ ID NO:2 and inhibits serine protease activity, as well as isolated mammalian CAP-3 protein homologous to the amino acid sequence of SEQ ID NO:4. In exemplary embodiments described herein the CAP-2 and CAP-3 proteins are human, e.g., the protein of SEQ ID NO: 2 or SEQ ID NO:4, or an allelic variant thereof.

In other embodiments the invention provides expression vectors having as operably linked elements a transcriptional promoter, a DNA segment encoding a mammalian CAP-2 or CAP-3 protein wherein said protein is homologous to the amino acid sequence depicted in SEQ ID NO:2 or SEQ ID NO:4 or an allelic variant, and inhibits serine protease activity, and a transcriptional terminator. Cultured host cells are also provided which are transformed or transfected with these expression vectors. Preferably the host cell is a mammalian cell.

In other aspects the invention provides methods for purifying a protein in a solution which contains a protease. The solution containing the protein of interest is exposed to a mammalian CAP-2 or a CAP-3 serine protease inhibitor, for example, that which has been immobilized to an affinity column, whereby the protease binds to the inhibitor and the activity of the protease is inhibited. One or more subsequent separation or purification steps can be performed in the presence of said serine protease inhibitor to obtain said purified protein.

In another embodiment methods are provided for producing a mammalian CAP-2 or CAP-3 polypeptide by growing eukaryotic cells, especially mammalian cells, transformed or transfected with a DNA construct which comprises an operably linked transcriptional promoter, a DNA segment encoding a mammalian CAP-2 or CAP-3 polypeptide which inhibits serine protease activity, and a transcriptional terminator. The CAP-2 or CAP-3 polypeptide is preferably homologous to the amino acid sequence of SEQ ID NO:2 or SEQ ID No:4, respectively. The cells are cultured under conditions whereby the CAP-2 or CAP-3 encoding DNA segment is expressed. The mammalian CAP-2 or CAP-3 polypeptide can then be isolated from the host cells, e.g., by affinity purification or similar procedure.

DESCRIPTION OF THE SPECIFIC EMBODIMENTS

The present invention provides for isolated cytoplasmic antiproteinase-2 (CAP-2) proteins, for isolated cytoplasmic antiproteinase-3 (CAP-3) proteins, polypeptides thereof, and for isolated nucleic acids encoding these proteins and polypeptides. The isolated CAP-2 and CAP-3 nucleic acid and protein compositions can be used in a number of applications. For instance, protease degradation during protein purification is a common problem in protein chemistry. CAP-2 and CAP-3 serpins can be used in the purification of a variety of proteins, including those of known importance in medicine and industry. As described herein, CAP-2 and CAP-3 nucleic acid and protein compositions are also useful in the treatment of inflammatory diseases and in the treatment of diseases involving apoptosis. In addition, these compositions can be used in in vitro diagnostic procedures for these diseases.

By "isolated" CAP-2 or CAP-3 is meant to refer to CAP-2 or CAP-3 which is in other than its native environment, and includes, for example, substantially purified CAP-2 and CAP-3 as defined herein. More generally, isolated is meant to include CAP-2 or CAP-3 as a heterologous component of a cell or other system. For example, CAP-2 or CAP-3 may be expressed by a cell transfected with a DNA construct which encodes CAP-2 or CAP-3, and then separated from the cell. Thus, in this context, the environment of isolated CAP-2 or CAP-3 is not as it occurs in its native state, particularly when it is present in a system as an exogenous component.

The predicted amino acid sequences of human CAP-2 and CAP-3 proteins are depicted in Seq. ID No. 2 and Seq. ID No. 4, respectively. The predicted amino acid sequences of CAP-2 and CAP-3 are 374 and 376 amino acids, respectively. Both human proteins have a predicted molecular weight of about 42 kDa.

Human CAP-2 and CAP-3 proteins share some amino acid sequence identity with other members of the ovalbumin branch of the serpin super family of proteinase inhibitors. Relatedness between these group of proteins was calculated using the NBRF ALIGN program. Using this program, the CAP-2 and CAP-3 human proteins have 68% and 63% identity, respectively, with the human cytoplasmic antiproteinase (CAP-1) protein sequence isolated from human placenta. Morgenstern et al., *Biochem.* 33:3432–3441 (1994). In addition, CAP-2 shows 63% amino acid sequence identity to CAP-3. Human CAP-2 and CAP-3 also exhibit a degree of amino acid sequence identity to other human members of the ovalbumin family of cytoplasmic serpins. For instance, CAP-2 has 51% identity and CAP-3 has 49% identity with elastase inhibitor. CAP-2 and CAP-3 have 46% and 45% identity with plasminogen activator inhibitor-2, respectively. In addition, CAP-2 has 46% identity and CAP-3 has 45% identity with squamous cell carcinoma antigen.

CAP-2 and CAP-3 lack a typical N-terminal clearable signal sequence that is present in many other members of the serpin super-family. CAP-2 and CAP-3 also lack a C-terminal extension which is present in many serpins. CAP-2 and CAP-3 both have a serine corresponding to position 375 of $\alpha_1$-proteinase inhibitor in place of a highly conserved Asn found among the serpins distantly related to the ovalbumin family. CAP-1 and CAP-2 also have potential N-glycosylation consensus motifs (N-X-T/S) starting at $Asn^8$ and $Asn^{78}$ of CAP-2 and $Asn^6$ and $Asn^{23}$ of CAP-3.

CAP-2 polypeptides typically show substantial sequence identity or homology to the amino acid sequence of Seq ID No. 2. Similarly, CAP-3 polypeptides typically show substantial sequence identity to the amino acid sequence of Seq. ID No. 4. As applied to these polypeptides and peptides thereof, the terms "substantial sequence identity" or "homology" or "homologous" mean that two amino acid sequences, when optimally aligned, such as by the programs GAP or BESTFIT using default gap penalties, share at least 80 percent sequence identity, preferably at least 90 percent sequence identity, more preferably at least 95 percent sequence identity or more. "Percentage amino acid identity" or "percentage amino acid sequence identity" refers to a comparison of the amino acids of two polypeptides which, when optimally aligned, have approximately the designated percentage of the same amino acids. Preferably, residue positions which are not identical differ by conservative amino acid substitutions. For example, the substitution of amino acids having similar chemical properties such as charge or polarity are not likely to substantially effect the properties of a protein. Examples include glutamine for asparagine or glutamic acid for asptatic acid.

The terms "CAP-2 protein" and "CAP-3 protein" refer not only to the amino acid sequences disclosed herein, but also to other proteins that are allelic or species variants of these amino acid sequences. It is also understood that these terms include nonnatural mutations introduced by deliberate mutation using recombinant technology such as single site mutation or by excising short sections of DNA encoding CAP-2 or CAP-3 proteins or by substituting new amino acids or adding new amino acids. Such minor alterations substantially maintain the immunoidentity of the original molecule and/or its biological activity. The biological properties of the altered proteins can be determined by expressing the protein in an appropriate cell line and by determining the ability of the protein to inhibit designated serine proteases. The biological activity of CAP-2 can be determined by its ability to inhibit serine proteases, for example, those with trypsin-like specificity. The biological activity of CAP-3 can be determined, for example, by its ability to inhibit proteases in the ICE family. Particular protein modifications considered minor would include substitution of amino acids of similar chemical properties, e.g., glutamic acid for aspartic acid or glutamine for asparagine.

By aligning a protein optimally with the protein of Seq. ID No. 2 or Seq. ID No. 4, and by using immunoassays as described herein to determine immunoidentity, one can readily determine the protein compositions of the invention. For example, CAP-2 proteins from different mammalian species, e.g., other primate species, are typically specifically immunoreactive with antibodies raised to the CAP-2 protein depicted in Seq. ID No. 2, whereas CAP-3 proteins from different mammalian species, e.g., other primate species, are typically specifically immunoreactive with antibodies raised to the CAP-3 protein depicted in Seq. ID No. 4.

In other embodiments the present invention provides isolated nucleic acid molecules which encode the CAP-2 or CAP-3 proteins. The term "isolated" as applied to nucleic acid molecules means those which are separated from their native environment, and preferably free of non-CAP-2 or non-CAP-3 DNA or coding sequences with which they are naturally associated. The term "nucleic acids", as used herein, refers to either DNA or RNA. "Nucleic acid molecule" or "polynucleotide sequence" refers to a single—or double-stranded polymer of deoxyribonucleotide or ribonucleotide bases read from the 5' to the 3'end. The nucleic acid molecules of the invention, whether RNA, cDNA, or genomic DNA, may be isolated from natural sources or may be prepared in vitro. The nucleic acids may be present in transformed or transfected whole cells, in a transformed or transfected cell lysate, or in a partially purified or substantially pure form.

The nucleic acid molecules of the invention are typically identical to or show substantial sequence identity or homology (determined as described herein) to the nucleic acid molecules having sequences of Seq ID. Nos. 1 and 3 or the complements thereof. The nucleic acid molecules include those which are equivalent to native or allelic sequences due to the degeneracy of the genetic code as well as sequences which are introduced to provide codon preference in a specific host cell. Nucleic acids encoding mammalian CAP-2 and CAP-3 proteins will typically hybridize to the nucleic acid sequences of Seq. ID No. 1 or Seq. ID No. 3, respectively, under stringent hybridization conditions. Less stringent hybridization conditions may also be selected. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one. Thus, the phrase "selectively hybridizing to" refers to a nucleic acid probe that hybridizes, duplexes or binds preferentially to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. For discussions of nucleic acid probe design and annealing conditions, see, for example, Sambrook et al., *Molecular Cloning*: A Laboratory Manual (2nd ed.), Vols. 1–3, Cold Spring Harbor Laboratory, (1989) or *Current Protocols in Molecular Biology*, F. Ausubel et al., ed., Greene Publishing and Wiley-Interscience, New York (1987), each of which is incorporated herein by reference.

Techniques for manipulation of nucleic acids encoding CAP-2 and CAP-3 proteins such as subcloning nucleic acid sequences encoding polypeptides into expression vectors, labelling probes, DNA hybridization, and the like are described generally in Sambrook, supra.

There are various methods of isolating nucleic acid molecules encoding CAP-2 or CAP-3 proteins. For example, DNA is isolated from a genomic or cDNA library using labeled oligonucleotide probes having sequences complementary to the sequences disclosed herein (Seq. ID No. 1 and Seq. ID No. 3). Full-length probes may be used, or oligonucleotide probes may also be generated by comparison of the sequences of Seq. ID Nos. 1 and 3. Such probes can be used directly in hybridization assays to isolate DNA encoding CAP-2 or CAP-3 proteins. Alternatively, probes can be designed for use in amplification techniques such as PCR (Mullis et al., U.S. Pat. Nos. 4,683,195 and 4,683,202, incorporated herein by reference), and DNA encoding CAP-2 and CAP-3 proteins may be isolated by using methods such as PCR. Nucleic acid probes may be DNA or RNA fragments. DNA fragments can be prepared, for example, by digesting plasmid DNA, or by use of PCR, or synthesized by either the phosphoramidite method described by Beaucage and Carruthers, *Tetrahedron Lett.* 22:1859–1862 (1981), or by the triester method according to Matteucci, et al., *J. Am. Cham. Soc.*, 103:3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

To prepare a cDNA library, mRNA is isolated from tissue such as human placenta which expresses CAP-2 or CAP-3 protein. cDNA is prepared from the mRNA and ligated into a recombinant vector. The vector is transfected into a recombinant host for propagation, screening and cloning. Methods for making and screening cDNA libraries are well known. See Gubler and Hoffman, *Gens* 25:263–269 (1983) and Sambrook, et al., supra.

For a genomic library, the DNA is extracted from tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro, as described in Sambrook, et al. Recombinant phage are analyzed by plaque hybridization as described in, e.g., Benton and Davis, Science, 196:180–182 (1977). Colony hybridization is carried out as generally described in, e.g., Grunstein et al. *Proc. Natl. Acad. Sci. USA*, 72:3961–3965 (1975).

DNA encoding a CAP-2 or CAP-3 protein is identified in either cDNA or genomic libraries by its ability to hybridize with nucleic acid probes, for example on Southern blots, and these DNA regions are isolated by standard methods familiar to those of skill in the art. See Sambrook, et al.

Various methods of amplifying target sequences, such as the polymerass chain reaction, can also be used to prepare nucleic acids encoding CAP-2 or CAP-3 proteins. PCR technology is used to amplify such nucleic acid sequences directly from mRNA, from cDNA, and from genomic libraries or cDNA libraries. The isolated sequences encoding CAP-2 or CAP-3 proteins may also be used as templates for PCR amplification.

In PCR techniques, oligonucleotide primers complementary to the two 3' borders of the DNA region to be amplified are synthesized. The polymerass chain reaction is then carried out using the two primers. See *PCR Protocols: A Guide to Methods and Applications*. Innis, M., Gelfand, D., Sninsky, J. and White, T., eds., Academic Press, San Diego (1990). Primers can be selected to amplify the entire regions encoding a full-length CAP-2 or CAP-3 protein or to amplify smaller DNA segments as desired.

PCR can be used in a variety of protocols to isolate cDNAs encoding CAP-2 or CAP-3 proteins. In these protocols, appropriate primers and probes for amplifying DNA encoding CAP-2 or CAP-3 proteins are generated from analysis of the DNA sequences listed herein. Once such regions are PCR-amplified, they can be sequenced and oligonucleotide probes can be prepared from sequence obtained. These probes can then be used to isolate DNA's encoding CAP-2 or CAP-3 proteins, similar to the procedure used in example 2 herein. CAP-2 and CAP-3 proteins can be isolated from a variety of different tissues using this procedure.

Oligonucleotides for use as probes are chemically synthesized according to the solid phase phosphoramidite triester method first described by Beaucage and Carruthers, *Tetrahedron Lett.*, 22:1859–1862 (1981), using an automated synthesizer, e.g., as described in Needham-VanDevanter, et al., *Nucleic Acids Res.*, 12:6159–6168 (1984). Purification of oligonucleotides is by either native acrylamide gel electrophoresis or by anion-exchange HPLC as described in Pearson and Regnier, *J. Chrom.*, 255:137–149

(1983). The sequence of the synthetic oligonucleotide can be verified using the chemical degradation method of Maxam and Gilbert, *Meth. Enzymol.*, 65:499–560 (1984).

Other methods known to those of skill in the art may also be used to isolate DNA molecules encoding CAP-2 or CAP-3 proteins. See Sambrook, et al. for a description of other techniques for the isolation of DNA encoding specific protein molecules. Thus, the present invention includes nucleotide sequences that have substantial sequence identity or homology to the CAP-2 and CAP-3 nucleotide sequences described in SEQ ID NOs 2 and 4. For substantial sequence identity or homology the polynucleotide comprises a sequence that has at least 80 percent sequence identity, preferably at least 90 percent sequence identity, and more preferably at least 95 percent sequence identity. The comparison is made to a reference sequence over a comparison window of at least 20 nucleotide positions, frequently over a window of at least 25–50 nucleotides, wherein the percentage of sequence identity is calculated by comparing the reference sequence to the polynucleotide sequence, which may include deletions or additions which total 20 percent or less of the reference sequence over the window of comparison. The reference sequence may be a subset of a larger sequence, for example, as a segment of the human CAP-2 or CAP-3 sequences described herein. Optimal alignment of sequences for aligning a comparison window may be conducted according to the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci.* (USA) 85:2444, or by computerized implementations of these algorithms (GAP, BESTFIT, FASTA, and TFASTA in the Wisconsin Genetics Software Package Release 7.0, Genetics Computer Group, 575 Science Dr., Madison, Wis.).

Once DNA encoding CAP-2 or CAP-3 proteins or a homologous sequence is isolated and cloned, CAP-2 or CAP-3 proteins or a homologous protein can be expressed in a variety of recombinantly engineered cells. Numerous expression systems are available for expression of DNA encoding CAP-2 or CAP-3 proteins. The expression of natural or synthetic nucleic acids encoding CAP-2 or CAP-3 proteins will typically be achieved by operably linking the DNA to a promoter (which is either constitutive or inducible) within an expression vector. By expression vector is meant a DNA molecule, linear or circular, that comprises a segment encoding a CAP-2 or CAP-3 protein or polypeptide of interest, operably linked to additional segments that provide for its transcription. Such additional segments include promoter and terminator sequences. An expression vector may also include one or more origins of replication, one or more selectable markers, an enhancer, a polyadenylation signal, etc. Expression vectors are generally derived from plasmid or viral DNA, or may contain elements of both. The term "operably linked" indicates that the segments are arranged so that they function in concert for their intended purposes, e.g., transcription initiates in the promoter and proceeds through the coding segment to the terminator. See Sambrook et al., supra.

A variety of procaryotic expression systems may be used to express CAP-2 or CAP-3 proteins. Examples include E. coli, Bacillus, Streptomyces, and the like. For example, CAP-2 and CAP-3 proteins may be expressed in *E. coli*.

Expression vectors can be constructed which contain a promoter to direct transcription, a ribosome binding site, and a transcriptional terminator. Examples of regulatory regions suitable for this purpose in *E. coli* are the promoter and operator region of the *E. coli* tryptophan biosynthetic pathway as described by Yanofsky, *J. Bacteriol.*, 158:1018–1024 (1984) and the leftward promoter of phage lambda (P$\lambda$) as described by Herskowitz and Hagen, *Ann. Rev. Genet.*, 14:399–445 (1980). The inclusion of selection markers in DNA vectors transformed in *E. coli* is also useful. Examples of such markers include genes specifying resistance to ampicillin, tetracycline, or chloramphenicol. Vectors used for expressing foreign genes in bacterial hosts will generally contain a selectable marker, such as a gene for antibiotic resistance, and a promoter which functions in the host cell. Plasmids useful for transforming bacteria include pBR322 (Bolivar et al., *Gene* 2:95–113 (1977)), the pUC plasmids (*Messing, Meth. Enzymol.* 101:20–77 (1983), Vieira and Messing, *Gene* 19:259–268 (1982)), pCQV2 (Queen, ibid.), and derivatives thereof. Plasmids may contain both vital and bacterial elements. Methods for the recovery of the proteins in biologically active form are discussed in U.S. Pat. Nos. 4,966,963 and 4,999,422, which are incorporated herein by reference. See Sambrook, et al. for a description of other prokaryotic expression systems.

CAP-2 or CAP-3 proteins produced by prokaryotic cells may not necessarily fold properly. During purification from *E. coli*, the expressed protein may first be denatured and then renatured. This can be accomplished by solubilizing the bacterially produced proteins in a chaotropic agent such as guanidine HCl and reducing all the cysteine residues with a reducing agent such as beta-mercaptoethanol. The protein is then renatured, either by slow dialysis or by gel filtration. See U.S. Pat. No. 4,511,503, incorporated herein by reference. Detection of the expressed protein is achieved by methods such as radioimmunoassay, Western blotting techniques or immunoprecipitation.

For expression in eukaryotes, host cells for use in practicing the present invention include mammalian, avian, plant, insect, and fungal cells. Fungal cells, including species of yeast (e.g., Saccharomyces spp., Schizosaccharomyces spp.) or filamentous fungi (e.g., Aspergillus spp., Neurospora spp.) may be used as host cells within the present invention. Strains of the yeast *Saccahromyces cerevlsiae* can be used. As explained briefly below, CAP-2 and CAP-3 proteins can be expressed in these eukaryotic systems.

Recombinantly produced CAP-2 or CAP-3 proteins can be directed into the secretory pathway of the host cell in order to facilitate purification, by using at least one signal sequence operably linked to the DNA sequence of interest. Examples of such signals include the alpha factor signal sequence (pre-pro sequence; Kurjan and Herskowitz, *Cell* 30: 933–943 (1982); Kurjan et al., U.S. Pat. No. 4,546,082; Brake, U.S. Pat. No. 4,870,008), the PH05 signal sequence (Beck et al., WO 86/00637), the BAR1 secretory signal sequence (MacKay et al., U.S. Pat. No. 4,613,572; MacKay, WO 87/002670), the SUC2 signal sequence (Carlson et al., *Mol. Cell. Biol.* 3:439–447 (1983)), the $\alpha$-1-antitrypsin signal sequence (Kurachi et al., *Proc. Natl. Acad. Sci. USA* 78: 6826–6830 (1981)), the $\alpha$-2 plasmin inhibitor signal sequence (Tone et al., J. Biochem. (Tokyo) 102:1033–1042 (1987)) and the tissue plasminogen activator leader sequence (Pennica et al., *Nature* 301:214–221 (1983)). Alternatively, a secretory signal sequence may be synthesized according to the rules established, for example, by yon Heinje (*Eur. J. Biochem.* 133: 17–21 (1983); *J. Mol. Biol.* 184:99–105, (1985); *Nuc. Acids Res.* 14:4683–4690 (1986)).

Signal sequences may be used singly or may be combined. For example, a first signal sequence may be used singly or in combination with a sequence encoding the third domain of Barrier (described in U.S. Pat. No. 5,037,743, incorporated by reference herein in its entirety). A DNA segment encoding the third domain of Barrier may be positioned in proper reading frame 3' of the CAP-2 or CAP-3 DNA sequence of interest or 5' to the DNA sequence and in proper reading frame with both the signal sequence and the CAP-2 or CAP-3 DNA sequence of interest.

Suitable yeast vectors for use in the present invention include YRp7 (Struhl et al., *Proc. Natl. Acad. Sci. USA* 76:1035–1039 (1978)), YEp13 (Broach et al., *Gens* 8: 121–133 (1979)), POT vectors (Kawasaki et al, U.S. Pat. No. 4,931,373, which is incorporated by reference herein), pJDB249 and pJDB219 (Beggs, *Nature* 275:104–108 (1978)) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al., ibid. ), URA3 (Botstein et al., *Gene* 8:17 (1979)), HIS3 (Struhl et al., ibid. ) or POT1 (Kawasaki et al., ibid.). Another suitable selectable marker is the CAT gene, which confers chloramphenicol resistance on yeast cells.

Examples of promoters for use in yeast include promoters from yeast glycolytic genes (Hitzeman et al., *J. Biol. Chem.* 255:12073–12080 (1980); Alber and Kawasaki, *J. Mol. Appl. Genet.* 1:419–434 (1982); Kawasaki, U.S. Pat. No. 4,599,311) or alcohol dehydrogenase genes (Young et al., in *Genetic Engineering of Microorganisms for Chemicals*, Hollaender et al., (eds.), p. 355, Plenum, N.Y. (1982); Ammerer, *Meth. Enzymol.* 101:192–201 (1983)). The TPI1 promoter (Kawasaki, U.S. Pat. No. 4,599,311, 1986) and the ADH2-4$^c$ promoter (Russell et al., *Nature* 304:652–654 (1983); and EP 284,044 can also be used. The expression units may also include a transcriptional terminator. An example of such a transcriptional terminator is the TPI1 terminator (Alber and Kawasaki, ibid.).

In addition to yeast, proteins of the present invention can be expressed in filamentous fungi, for example, strains of the fungi Aspergillus (McKnight et al., U.S. Pat. No. 4,935,349, which is incorporated herein by reference). Examples of useful promoters include those derived from Aspergillus nidulans glycolytic genes, such as the ADH3 promoter (McKnight et al., *EMBO J.* 4:2093–2099 (1985)) and the tpiA promoter. An example of a suitable terminator is the ADH3 terminator (McKnight et al., ibid. ). The expression units utilizing such components are cloned into vectors that are capable of insertion into the chromosomal DNA of Aspergillus.

Techniques for transforming fungi are well known in the literature, and have been described, for instance, by Beggs (ibid.), Hinnen et al. (*Proc. Natl. Acad. Sci. USA* 75: 1929–1933 (1978)), Yelton et al. (*Proc. Natl. Acad. Sci. USA* 81:1740–1747 (1984)), and Russell (*Nature* 301:167–169 (1983)). The genotype of the host cell will generally contain a genetic defect that is complemented by the selectable marker present on the expression vector. Choice of a particular host and selectable marker is well within the level of ordinary skill in the art.

In addition to fungal cells, cultured mammalian cells may be used as host cells within the present invention. Examples of cultured mammalian cells for use in the present invention include the COS-1 (ATCC CRL 1650), BHK, and 293 (ATCC CRL 1573; Graham et al., *J. Gen. Virol.* 6:59–72 (1977)) cell lines. An example of a BHK cell line is the BHK 570 cell line (deposited with the American Type Culture Collection under accession number CRL 10314). In addition, a number of other mammalian cell lines may be used within the present invention, including Rat Hep I (ATCC CRL 1600), Rat Hep II (ATCC CRL 1548), TCMK (ATCC CCL 139), Human lung (ATCC CCL 75.1), Human hepatoma (ATCC HTB-52), Hep G2 (ATCC HB 8065), Mouse liver (ATCC CCL 29.1), NCTC 1469 (ATCC CCL 9.1) and DUKX cells (Urlaub and Chasin, *Proc. Natl. Acad. Sci USA* 77: 4216–4220 (1980)).

Mammalian expression vectors for use in carrying out the present invention will include a promoter capable of directing the transcription of a cloned gene or cDNA. Both viral promoters or cellular promoters can be used. Viral promoters include the immediate early cytomegalovirus promoter (Boshart et al., *Cell* 41:521–530 (1985)) and the SV40 promoter (Subramani et al., *Mol. Cell. Biol.* 1:854–864 (1981)). Cellular promoters include the mouse metallothionein-1 promoter (Palmiter et al., U.S. Pat. No. 4,579,821), a mouse $V_K$ promoter (Bergman et al., *Proc. Natl. Acad. Sci. USA* 81:7041–7045 (1983); Grant et al., *Nuc. Acids Res.* 15:5496 (1987)), a mouse $V_H$ promoter (Loh et al., *Cell* 33:85–93 (1983)), and the major late promoter from Adenovirus 2 (Kaufman and Sharp, *Mol. Cell. Biol.* 2:1304–13199 (1982)). Such expression vectors can also contain a set of RNA splice sites located downstream from the promoter and upstream from the DNA sequence encoding the peptide or protein of interest. RNA splice sites may be obtained from adenovirus and/or immunoglobulin genes. Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9:3719–3730 (1981)). The expression vectors can include a noncoding viral leader sequence, such as the Adenovirus 2 tripartite leader, located between the promoter and the RNA splice sites. Preferred vectors may also include enhancer sequences, such as the SV40 enhancer and the mouse μ enhancer (Gillies, *Cell* 33: 717–728 (1983)). Expression vectors may also include sequences encoding the adenovirus VA RNAs.

Cloned DNA sequences can be introduced into cultured mammalian cells by, for example, calcium phosphate-mediated transfection (Wigler et al., *Cell* 14:725 (1978); Corsaro and Pearson, *Somatic Cell Genetics* 7:603 (1981); Graham and Van der Eb, Virology 52:456 (1973); which are incorporated by reference herein in their entirety). Other techniques for introducing cloned DNA sequences into mammalian cells may also be used, such as electroporation (Neumann et al., *EMBO J.* 1: 841–845 (1982)) or cationic lipid-mediated transfection (Hawley-Nelson et al., *Focus* 15:73–79 (1993)) using, e.g., a 3:1 liposome formulation of 2,3-dioleyloxy-N[2(sperminecarboxyamido)ethyl]-N,N-dimethyl-1-propanamintumtrifluoroacetate and dioleolyphosphatidylethanolamine in water (Lipofectamine™ reagent, GIBCO-BRL). To identify cells that have integrated the cloned DNA, a selectable marker is generally introduced into the cells along with the gene or cDNA of interest. Examples of selectable markers for use in cultured mammalian cells include genes that confer resistance to drugs, such as neomycin, hygromycin, and methotrexate. The selectable marker can be an amplifiable selectable marker. A preferred amplifiable selectable marker is the DHFR gene. Selectable markers are reviewed by Thilly (*Mammalian Cell*

*Technology*, Butterworth Publishers, Stoneham, Mass., which is incorporated herein by reference). The choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA" to the mixture which is introduced into the cells.

Transfected mammalian cells are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

Promoters, terminators and methods useful for introducing expression vectors encoding CAP-2 or CAP-3 proteins of the present invention into plant, avian and insect cells have been described in the art. The use of baculoviruses, for example, as vectors for expressing heterologous DNA sequences in insect cells has been reviewed by Atkinson et al. (Pestic. Sci. 28:215–224 (1990)). The use of *Agrobacterium rhizogenes* as vectors for expressing genes in plant cells has been reviewed by Sinkar et al. (*J. Biosci. (Bangalore)* 11:47–58 (1987)).

Host cells containing DNA constructs of the present invention are then cultured to produce CAP-2 or CAP-3 proteins. The cells are cultured according to standard methods in a culture medium containing nutrients retired for growth of the host cells. A variety of suitable media are known in the art and generally include a carbon source, a nitrogen source, essential amino acids, vitamins, minerals and growth factors. The growth medium will generally select for cells containing the DNA construct by, for example, drug selection or deficiency in an essential nutrient which is complemented by the selectable marker on the DNA construct or co-transfected with the DNA construct.

The polypeptides of the invention, including recombinantly produced CAP-2 and CAP-3 proteins produced as described above, may be purified by techniques well known to those of skill in the art. For example, recombinantly produced CAP-2 or CAP-3 polypeptides can be directly expressed or expressed as fusion proteins. The proteins can then be purified by a combination of cell lysis (e.g., sonication) and affinity chromatography. For fusion products, subsequent digestion of the fusion protein with an appropriate proteolytic enzyme releases the desired polypeptide.

The phrase "substantially purified" when referring to CAP-2 or CAP-3 peptides or proteins of the present invention, means a composition which is essentially free of other cellular components with which the CAP-2 or CAP-3 peptides or proteins are associated in their native environment. Purified protein is preferably in a homogeneous state although it can be in either a dry or aqueous solution. Purity and homogeneity are typically determined using analytical chemistry techniques such as polyacrylamide gel electrophoresis or high performance liquid chromatography. Generally, a substantially purified protein will comprise more than 80% of all macromolecular species present in the preparation. Preferably, the protein is purified to represent greater than 90% of all proteins present. More preferably the protein is purified to greater than 95%, and most preferably the protein is purified to essential homogeneity, wherein other macromolecular species are not detected by conventional techniques.

The CAP-2 and CAP-3 peptides and proteins of the present invention may be purified to substantial purity by standard techniques well known in the art, including selective precipitation with such substances as ammonium sulfate; column chromatography; affinity methods, including immunopurification methods; and others. See, for instance, R. Scopes, *Protein Purification: Principles and Practice*, Springer-Verlag: New York (1982), incorporated herein by reference. For example, antibodies may be raised to the CAP-2 or CAP-3 protein as described herein. CAP-2 or CAP-3 protein can be extracted from tissues or cell cultures that express the protein and then immunoprecipitated. The CAP-2 or CAP-3 protein may then be further purified by standard protein chemistry techniques as described above.

The CAP-2 and CAP-3 of the present invention find use as protease inhibitors in the purification of a wide variety of different proteins. Proteolysis is a major problem in purification of proteins. Proteolysis can occur at all stages of purification, particularly the early stages, when more contaminating proteins are present. Because of their widespread distribution, serine proteases often contribute to the degradation of proteins during purification. Several different serine protease inhibitors have successfully been used, along with other protease inhibitors, during the purification of variety of different proteins. (See, e.g., Deutscher, *Meth. Enzymol.*, 182:83–89 (1990)). Isolated CAP-2 or CAP-3 proteins can be used alone or in combination with a number of other protease inhibitors. CAP-2 or CAP-3 is used as a serine protease inhibitor at a concentration of about 10 ng-100 µg/ml, typically about 1 µg/ml.

Within one embodiment, CAP-2 or CAP-3 is covalently coupled to a solid support using conventional coupling chemistry. Suitable supports in this regard include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins through amino groups, carboxyl groups, sulphydryl groups, hydroxyl groups and/or carbohydrate moieties. Examples of coupling chemistries include cyanogen bromide activation, N-hydroxysuccinimide activation, epoxide activation, sulphydryl activation, hydrazide activation, and carboxyl and amino derivatives for carbodiimide coupling chemistries. In a typical procedure, the resin-CAP complex is packed into a column, and an aqueous mixture containing a protease is applied to the column. In general, the mixture will be buffered at a pH compatible with the activity optimum of the protease to maximize binding of the protease to the CAP protein. The protease is allowed to bind to the immobilized CAP, and other components of the mixture pass through the column. The column is washed at the pH of the loading buffer to remove additional unbound mixture components. The bound protease can be eluted from the column with buffers that disrupt protein-protein interactions, such as chaotropic salts (KSCN, etc.) or high or low pH solutions. These general methods can be readily adapted for purification of proteases or removal of proteases from process streams.

The specificity of CAP-2 and CAP-3 for inhibition of different serine proteases can be determined using a variety of methods. For example, isolated biologically active CAP-2 or CAP-3 protein is added to an enzymatically active preparation of the selected serine protease, and enzyme activity is monitored to detect inhibition. For example, specificity and kinetics of inhibition for trypsin-like serine proteases can be determined as described in Morgenstern, et al., *Biochem.* 33:3432–3441 (1994), incorporated herein by reference. As an additional example, specificity for inhibition of other proteases of interest, such as those in the ICE family, is determined by adding CAP-2 and CAP-3 to preparations of these enzymes in vitro and monitoring changes in enzyme activity.

Pharmacological activity of CAP-2 and CAP-3 and agonists or antagonists thereof can also be determined in animal model systems known to those of skill in the art. For example, CAP-2 or CAP-3 may inhibit inflammation by inhibiting the activity of ICE or other serine proteases involved in the inflammation process. A number of in vitro and animal model systems are used for identification of compounds with anti-inflammatory activity. For example, cultured vertebrate dorsal root ganglion (DRG) neurons can be transfected with an expression vector which encodes CAP-2 or CAP-3 cDNA, and the inhibition of cell death or degeneration determined, as generally described in Gagliardini et al., *Science* 263:826–828 (1994), incorporated herein by reference. The effect of CAP-2 or CAP-3 and antagonists or agonists thereof can be demonstrated by other methods, e.g, transfecting Ice, Ich-1L, or other gene which induces programmed cell death or cell degeneration (e.g., ced-3) into a cell which is also transfected with a gene encoding CAP-2 or CAP-3, such as DRG, RAT-1 or HeLa cells, and exposing the cells to the potential CAP-2 or CAP-3 agonist or antagonist compound or gene expressing said compound. See generally, Miura et al., *Cell* 75:653–660 (1993) and Wang et al., *Cell* 78:739–750 (1994), each of which is incorporated herein by reference.

The CAP-2 and CAP-3 of the present invention also have a variety of in vitro diagnostic uses. For example, CAP-2 may be an endogenous inhibitor of specific trypsin-like serine proteases, and CAP-3 may be an endogenous inhibitor for members of the ICE family of proteases including Ich-1. Proteases with trypsin-like specificity are involved in many physiologically important processes, and ICE and Ich-1 play important roles in inflammation and apoptosis, respectively. Because of this, determination of CAP-2 or CAP-3 in biological samples can be useful in medicine.

Levels of CAP-2 or CAP-3 protein can be determined, for example, by means of a variety of different immunoassay procedures. Antibodies, both polyclonal and monoclonal, can be produced to CAP-2 and CAP-3 proteins and polypeptide fragments thereof according to general procedures set forth in Harlow and Lane, *Antibodies: A Laboratory Manual*, Cold Spring Harbor Pubs., N.Y. (1988), incorporated herein by reference. Antibodies raised to a CAP-2 immunogen, e.g., that having the amino acid sequence depicted in Seq. ID No. 2, can be selected via screening procedures to be specifically immunoreactive with CAP-2 proteins and not with other proteins such as CAP-1 protein and CAP-3 protein. Similarly, antibodies raised to CAP-3 immunogen, e.g., that having the amino acid sequence depicted in Seq. ID No. 4, can be selected to be specifically immunoreactive with CAP-3 proteins and not with other proteins such as CAP-1 protein and CAP-2 protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane, supra, for a description of immunoassay formats and conditions that can be used to determine specific immunoreactivity.

Diagnostic immunoassays for CAP-2 or CAP-3 in a biological sample can be performed in a variety of different formats known to those of skill in the art and described in, e.g., Harlow and Lane, supra; *Basic and Clinical Immunology* 7th Edition (D. Stites and A. Terr ed.) 1991; *Enzyme Immunoassay*, E. T. Maggio, ed., CRC Press, Boca Raton, Fla. (1980); and "Practice and Theory of Enzyme Immunoassays, " P. Tijssen, *Laboratory Techniques in Biochemistry and Molecular Biology*, Elsevier Science Publishers B.V. Amsterdam (1985), each of which is incorporated herein by reference. By biological sample-is meant to include body fluids and tissue specimens, that is, any sample derived from or containing cells, cell components or cell products, including, but not limited to, cell culture supernatants, cell lysates, cleared cell lysates, cell extracts, tissue extracts, blood, plasma, serum, and fractions thereof.

Expression of mRNA encoding CAP-2 or CAP-3 proteins can be detected by various procedure involving nucleic acid hybridization. A variety of nucleic acid hybridization formats are known to those skilled in the art. For example, common formats include sandwich assays and competition or displacement assays. Hybridization techniques are generally described in "*Nucleic Acid Hybridization, A Practical Approach,*" Ed. Hames, B. D. and Higgins, S. J., IRL Press, 1985; Gall and Pardue (1969), *Proc. Natl. Acad. Sci., U.S.A.*, 63:378–383; and John et al., (1969) *Nature*, 223:582–587, and in Sambrook, et al. Hybridization techniques can be also used in methods such as restriction fragment length polymorphism (RFLP) analysis to detect the presence of genetic alterations in nucleic acids encoding CAP-2 and CAP-3 (see Sambrook, et al., Supra).

The CAP-2 and CAP-3 protein compositions of the present invention are useful in treatment and prevention of a variety of diseases, e.g., inflammatory diseases. The CAP-2 or CAP-3 composition is used to prevent neuronal degeneration. Inhibition of βIL-1 maturation indicates the subject composition can be used to treat Alzheimer's disease, arthritis, septic shock, head injury, and other inflammatory responses.

Pharmaceutical compositions of the invention are suitable for use in a variety of drug delivery systems. Pharmaceutically acceptable carriers and formulations for use in the present invention are found in *Remington's Pharmaceutical Sciences*, Mack Publishing Company, Philadelphia, Pa., 17th ed. (1985), which is incorporated herein by reference. For a brief review of methods for drug delivery, see Langer, *Science* 249:1527–1533 (1990), which is incorporated herein by reference.

In preparing pharmaceutical compositions of the present invention, it may be desirable to modify the compositions of the present invention to alter their pharmacokinetics and biodistribution. For a general discussion of pharmacokinetics, see *Remington's Pharmaceutical Sciences*, supra, Chapters 37–39. A number of methods for altering pharmacokinetics and biodistribution are known to one of ordinary skill in the art (See, e.g., Langer, supra). Examples of such methods include protection of the complexes in vesicles composed of substances such as proteins, lipids (for example, liposomes), carbohydrates, or synthetic polymers. For example, the complexes of the present invention may be incorporated into liposomes in order to enhance their pharmacokinetics and biodistribution characteristics. A variety of methods are available for preparing liposomes, as described in, e.g., Szoka et al., *Ann. Rev. Biophys. Bioeng.* 9:467 (1980), U.S. Pat. Nos. 4,235,871, 4,501,728 and 4,837,028, all of which are incorporated herein by reference.

The CAP-2 and CAP-3 proteins of the present invention can be used in pharmaceutical compositions that are useful for administration to mammals, including humans. The pharmaceutical compositions of the invention are intended for parenteral, topical, oral or local administration. For example, the pharmaceutical compositions can be administered parenterally, e.g., intravenously, subcutaneously, intradermally, or intramuscularly. The invention provides compositions that comprise a solution of the agents described above dissolved or suspended in an acceptable carrier, preferably an aqueous carrier. A variety of pharmaceutically acceptable aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain as pharmaceutically acceptable carriers, substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic pharmaceutically acceptable carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the pharmaceutical compositions containing the CAP-2 or CAP-3 proteins or peptide fragments thereof are preferably supplied in finely divided form along with a surfactant and propellant as pharmaceutically acceptable carriers. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides, may be employed. A carrier can also be included, as desired, as with, e.g., lecithin for intranasal delivery.

The pharmaceutical compositions of the invention can be administered in a variety of unit dosage forms depending upon the method of administration. For example, unit dosage forms suitable for oral administration include powder, tablets, pills, and capsules. The effective amount of the CAP-2 or CAP-3 protein in a pharmaceutical composition will depend on, e.g., the protein composition, the manner of administration, the weight and general state of health of the patient, the severity of the disease being treated and the judgment of the prescribing physician. Dosages, formulations and administration schedules may vary in these patients compared to normal individuals. In general, dosages range from about 100 µg to about 500 mg or more, with dosages of from about 250 µg to about 50 mg being more commonly used. It must be kept in mind that the materials of the present invention may generally be employed in serious disease or injury states, and in such cases it is possible and may be felt desirable by the treating physician to administer substantial excesses of these CAP-2 or CAP-3 compositions.

The following Examples are offered by way of illustration of the present invention, not limitation.

EXAMPLES

Example 1

Isolation of cDNA molecules encoding human CAP-2 and CAP-3 proteins
A. Generation of a nucleic acid probe for screening a human. cDNA library To isolate cDNA molecules encoding CAP-1 and CAP-2 proteins, a human placenta λgt11 cDNA library was screened using an antisense 209 base pair PCR-generated $^{32}$P-labeled probe corresponding to codons encoding residues 67–149 of the CAP-1 protein. (See Morgenstern et al. (1994) supra.) This probe was generated in a series of PCR reactions, as described below.

In the first PCR reaction, a human placenta cDNA library (Cat. #HL 1075b, ClonTech, Palo Alto, Calif.) was amplified using oligonucleotide ZC6657 (Seq. ID No. 5) and oligonucleotide ZC6658 (Seq. ID No. 6). These oligonucleotides are degenerate primers based on a peptide sequence isolated from the CAP-1 protein. (See Morgenstern et al. (1994) supra.) The PCR reaction was generated using Ampliwax™ (Roche Molecular Systems, Branchburg, N.J.) and a "hot start" technique that prevents false priming by adding the enzyme to the PCR reaction at an elevated temperature. More specifically, PCR was performed by mixing 21 µl H$_2$O, 8 µl dNTP (2.5 mM each dNTP), 8 µl of 20 pM/µl oligonucleotide ZC6657, 8 µl of 20 pM/µl oligonucleotide ZC6658, and 5 µl of 10×GeneAmp® PCR buffer. Ampliwax™ was added, and the reaction mixture was heated at 80° C. for 5 minutes and then at 35° C. for 2 minutes. After the wax hardened on top of the reaction mixture, 2 µl of the human placenta cDNA library was diluted into 42 µl of water and boiled 5–10 minutes. The diluted cDNA library was added above the cooled wax with 1 µl AmpliTaq® (5 units/µl; Roche) and 5 µl of 10× GeneAmp® PCR buffer (Roche). The reaction mixture was incubated for 30 cycles of the following temperatures: 95° C. for 30 seconds; 48° C. for 30 seconds; and 72° C. for 1 minute. This was followed by a 7 minute incubation at 72° C.

The product of the first PCR reaction was then used as a template in a second PCR reaction to generate a product of approximately 270 bp. A reaction mixture was prepared by combining 21 µl H$_2$O, 8 µl dNTPs (2.5 mM each), 8 µl of the ZC6657 oligonucleotide (20 pM/µl 8 µl of the ZC6658 oligonucleotide (20 pM/µl), and 5 µl of 10× GeneAmp® PCR buffer. Ampliwax™ was added, and the reaction mixture was heated at 80° C. for 5 minutes, then at 35° C. for 2 minutes. After the wax hardened, 43 µl H$_2$O, 1 µl AmpliTaq® (5 units/µl), 5 µl 10x GeneAmp® PCR buffer, and 1 µl template DNA were added above the cooled wax. The reaction mixture was then incubated for 30 cycles at the following temperatures: 95° C. for 30 seconds; 48° C. for 30 seconds; and 72° C. for 1 minute. This was followed by a 7 minute incubation at 72° C. The final PCR product was digested with EcoRI and ligated into the EcoRI digested vector ZEM 228CC, described below. The resulting construct was designated "clone 10 CAP-Zem228CC".

The vector Zem228CC was prepared from plasmid Zem228, a pUC18-based expression vector containing a unique Bam HI site for insertion of cloned DNA between the mouse metallothionein-1 promoter and SV40 transcription terminator and an expression unit containing the SV40 early promoter, neomycin resistance gene, and SV40 terminator. Zem228 was deposited with American Type Culture Collection, 12301 Parklawn Drive, Rockville, Md. on Sep. 28, 1993 as an *E. coli* HB101 transformant. It has been assigned Accession Number 69446. Plasmid Zem228 was modified to delete the two Eco RI sites by partial digestion with Eco RI, blunting with DNA polymerase I (Klenow fragment) in the presence of dNTPs, and re-ligation. Digestion of the resulting plasmid with Bam HI followed by ligation of the linearized plasmid with Bam Hi-Eco RI adapters resulted in a unique Eco RI cloning site. The resultant plasmid was designated Zem228R. The Sst I site between SV40 promoter and the mouse metallothionein-1 promoter was destroyed by linearizing Zem228R with Sst I, blunting the adhesive ends with T4 DNA polymerase in the presence of dNTPs and religating the linearized, blunt-ended fragment. A plasmid in which the Sst I site was destroyed was designed Zem228Ra.

To facilitate directional insertion of cDNA fragments into the vector, an adapter was synthesized which contained a 5' Eco RI adhesive end, an internal Sst I site and a 3' Eco RI adhesive end that does not regenerate an Eco RI site upon ligation with an Eco RI adhesive end. Plasmid Zem228Ra was linearized by digestion with Eco RI, and the linearized plasmid was treated with calf alkaline phosphatase to prevent recircularization. The linearized plasmid was ligated with kinased oligonucleotides ZC3169 and ZC3168 (see Table). A plasmid containing inserted adapter was designated Zem228C.

To improve the ability to achieve Eco RI+Sst I cleavage of the Zem228C vector, an oligonucleotide adapter was synthesized that contained an internal Eco RI site flanked by Eco RI adhesive ends that do not regenerate Eco RI sites upon ligation with Eco RI adhesive ends. Oligonucleotides ZC1773 and ZC1774 (Table) were kinased and annealed to form the adapter. Plasmid Zem228C was linearized by digestion with Eco RI, and the linearized vector and kinased adapter were ligated. A plasmid containing the adapter was confirmed and sequenced. Sequence analysis revealed that the plasmid contained a 30 bp DNA insert between the new Eco RI site and the downstream Sst I site. Since an Eco RI+Sst I cleavage of the vector prior to the insertion of a cDNA sequence removes the additional DNA sequence, the inserted DNA was not removed. The plasmid was designated Zem228CC.

mixture was incubated for 35 cycles at the following temperatures: 94° C. for 1 minute; 55° C. for 1 minute; and 72° C. for 1.5 minutes. This was followed by a 7 minute incubation at 72° C. The 210 bp product was labeled with $^{32}$P using a commercially available kit (Multi-prime kit, Amersham Corporation, Arlington Heights, Ill., USA).

B. Library screening and isolation and characterization of cDNA clones encoding human CAP-2 and CAP-3 proteins 33,000 phage from the human placenta cDNA library were plated on each of 23 plates to obtain 760,000 independent phage. Filter lifts were made from each plate using ICN BioTrans nylon membranes. Filters were prehybridized in 5×SSPE (20× SSPE is 175.3 g NaCl, 27.6 g NaH2PO4.H2O, 7.4 g EDTA, NaOH added to pH7.4 and water to 1 liter), 5× Denhardt's, 0.5% SDS, 100 µg/ml salmon sperm DNA at 65° C. for 6 hours. Filters were then hybridized in the above mixture with 1×10$^6$ cpm/ml of labeled CAP probe at 65° C. overnight. The filters were washed 3 times for 40 minutes each at room temperature in 0.2× SSC, 0.1% SDS, followed by 1 wash for 40 minutes at 65° C. Filters were exposed to X-ray film overnight. Two types of positive spots were observed: those which were extremely intense and corresponded to CAP cDNA, and those that gave much weaker signals.

For two of the weak signals, the corresponding phage were plaque-purified by additional rounds of hybridization and isolation using nitrocellulose filters. In some cases, filters were washed prior to hybridization in 5× SSC, 0.1% SDS at 65° C. for 1 hour; hybridization was carried out in 5× SSC at 56° C. overnight; and filters were washed at 58° C. in 2× SSC, 0.1% SDS. Two plaques were purified by this procedure. The two purified plaques were designated H2-2-11 and H3-1-11.

cDNA inserts were isolated from each purified plaque by PCR, using phage as a template and amplifying with oligonucleotide primers ZC2682 (Seq. ID No. 9) and ZC2683 (Seq. ID No.10), which anneal 5' and 3' to the EcoRI cloning site of λgt11. A 50 µl PCR reaction volume was used with 1 µl eluted phage, 40 pmoles of oligonucleotide ZC2682, 40 pmoles of oligonucleotide ZC2683, 5 µl 10× PFU buffer (Stratagene Cloning Systems, Stratagene, San Diego, Calif., USA), 5 µl dNTPs (2.5 mM each dNTP; Roche), and 1 µl PFU polymerase, 2.5 Units/µl (Stratagene, San Diego, Calif. USA). The reaction mixture was incubated for 35 cycles at the following temperatures: 94° C. for 1 minute; 60° C. for 1 minute; and 72° C. for 2 minutes. This was followed by a 7 minute incubation at 72° C. The resulting PCR products were designated H2-2-11 and H3-1-11.

The H2-2-11 and H3-1-11 PCR products were digested with EcoRI and individually ligated into the EcoRI site of pUC19. The H2-2-11 sequence was isolated as a 1.4 kb fragment. H3-1-11 contained an internal EcoRI site in the

TABLE

| | |
|---|---|
| ZC1773: | AATT AGGGAG ACCGGAATTC TGTGCTCTGT CAA (SEQ. ID No. 13) |
| ZC1774: | AATTTTGACA GAGCACAGAA TTCCGGTCTC CTT (SEQ. ID No. 14) |
| ZC3168: | AATT GAGCTC G (SEQ. ID No. 15) |
| ZC3169: | AATT CGAGCT C (SEQ. ID No. 16) |

The plasmid clone 10 CAP-Zem 228CC was used as a template to generate a probe for screening a human placenta cDNA library for nucleic acid sequences structurally related to CAP-1. A PCR reaction was carried out using the plasmid template and the oligonucleotide primers ZC6770 (Seq. ID No. 7) and ZC6771 (Seq. ID No. 8). PCR was performed in a 50 µl reaction volume with approximately 10 ng plasmid DNA, 40 pmoles of oligonucleotide ZC6770, 40 pmoles of oligonucleotide ZC6771, 5 µl of 10× GeneAmp® PCR buffer, 5 µl dNPS (2.5 mM each dNTP), and 0.25 µl AmpliTaq® DNA polymerase (5 Units/µl). The reaction cDNA, resulting in a 1.1 kb fragment and a 0.3 kb fragment upon digestion with EcoRI. Both cDNAs were sequenced and determined to be related to CAP-1 and other intracellular members of the serpin family of protease inhibitors. The nucleotide sequences and the deduced amino acid sequences of the inserts in clones H3-1-11 and H2-2-11 are shown in SEQ ID NO: 1-4. For both cDNAs, the active site region was sequenced from 2 independent PCR products to check for any PCR-generated errors.

The 5'-regions of both cDNAs contain a Kozak consensus sequence between nucleotide bases 110–119 of H2-2-11

(SEQ. ID. No. 3) and 88–97 of H3-1-11 (SEQ. ID. No. 1) that includes an in frame initiation codon. A second Kozak sequence also exists 117 nucleotide bases downstream of the first initiation codon and includes the codon for Met$^{41}$ of both proteins. The 3'-untranslated region of the H3-1-11 cDNA contains an AATAAA consensus sequence located 99 nucleotide bases downstream of the termination codon for nascent mRNA cleavage and polyadenylation. However, a polyadenylation consensus sequence was not found in the 3'-untranslated region of the H2-2-11 cDNA after sequencing 151 nucleotides downstream from the translational termination codon.

Alignment of the deduced primary structure of CAP-2 and CAP-3 with the amino acid sequences of CAP-1 and other human members of the ovalbumin serpin family identified the putative reactive center $P_1$–$P_1'$ residues of CAP-2 as $Arg^{341}$–$Cys^{342}$, respectively, which are identical to the CAP-1 reactive center residues. However, the regions flanking the $P_1$–$P_1'$ residues in CAP-1 and CAP-2 are highly divergent. The $P_2$–$P_6$ residues of CAP-1 and CAP-2 show no identity while $Arg^{346}$ in the $P_3'$ position was conserved in both serpins. Residues in the vicinity of $P_1$ have been previously shown to influence both proteinase target specificity and the inhibitory potency of several serpins. Carrell et al., Nature 353:576–578 (1991). Thus, this indicates that CAP-2 interacts with the active sites of distinct cognate proteinases that have trypsin-like substrate specificity. In contrast, alignment of the CAP-3 amino acid sequence identified the putative $P_1$_$P_1'$ residues at $Glu^{341}$–$Cys^{342}$, respectively.

The identification of an acidic $P_1$ residue in the CAP-3 reactive center is unique in the mammalian serpin superfamily. The only other serpin identified with an acidic $P_1$ residue in the reactive center is encoded by the crmA gene of the cowpox virus, which has been previously demonstrated to have a reactive center containing an Asp-Cys in the $P_1$–$P_1'$ positions, respectively. Furthermore, the crmA protein shows the greatest degree of amino acid sequence identity to the mammalian intracellular serpins of the ovalbumin family. By employing the NBRF program ALIGN, the crmA protein was found to share about 37% identity with CAP-2 and CAP-3. The CAP-3 reactive center domain shares about 54% of structurally conserved residues found in the reactive center domain of the crmA protein, including a conserved Asp to Glu switch in the $P_1$-specificity site. Moreover, the cytoplasmic antiproteinases have a unique Cys-residue conserved in the $P_1'$ position and found only in the corresponding position of the crmA serpin reactive center.

The crmA protein functions as a specific inhibitor of ICE which represents a prototype of a larger family of ICE-like homologs. The ICE family of cysteine proteinases have been linked to both the negative and positive regulation of apoptosis. A human homolog of ICE has been identified and designated as Ich-1. In contrast to ICE, Ich-1-mediated effects on apoptosis of Rat-1 cells is only partially blocked by either microinjected or coexpressed crmA protein. These findings suggest that Ich-1 and the crmA serpin interact weakly and further suggests that Ich-1 and ICE have distinct but overlapping substrate specificities.

Serp2-2, the cDNA encoding CAP-3 (H2-2-11), inserted into pUC19 as an EcoRI fragment; Serp3-1a (H3-1-11), the 5' EcoRI fragment of the CAP-2 clone inserted into pUC19; and Serp3-1b (H3-1-11), the 3' EcoRI fragment of the CAP-2 clone inserted into pUC19, were deposited with American Type Culture Collection, 12301 Parklawn Drive, Rockville, Md. on Oct. 6, 1994 as E. coli DH10b transformants and assigned Accession Numbers 69699, 69700, and 69701, respectively.

Example 2

Northern blot analysis of human tissues for expression of CAP-2 CAP-3 mRNA

To identify transcripts that encode CAP-2 and CAP-3 and determine their human tissue distribution, radiolabeled oligonucleotide probes corresponding to the reactive centers of these serpins were used to probe immobilized poly(A)+ mRNA by Northern analysis. A blot of poly(A)-containing mRNA from human tissues used a multiple tissue blot from CLONTECH Laboratories, Palo Alto, Calif., USA. The multiple tissue blot was probed with a 39-mer oligonucleotide corresponding to the reactive centers of the CAP homologs. The oligonucleotide used for CAP-2 has the following sequence: 5'-CTCCATTCTGCTGCACCGG-GAATTCCTGACCACAGCAGT-3'(Sequence ID No. 11). The oligonucleotide used for CAP-3 had the following sequence: 5'-AGATTCCATGCAGCACTCTGCAACTA-CAAAGCAGCTCGA-3'(Seq. ID No. 12). The oligonucleotide probes were 5'-labeled with [$^{32}$P$\gamma$]ATP (Dupont/NEN, Boston, Mass., USA) using T4 polynucleotide kinase (Promega Corporation, Madison, Wis., USA) to yield a specific activity of about 1–2×10$^8$ cpm/μg. Hybridization was performed at 55° C. in 5× SSPE, 2× Denhardt's, 0.5 SDS, 100 μg/ml salmon sperm DNA. The blots were washed at 57° C. in 2× SSC, 0.1% SDS and exposed to autoradiography.

The results indicated that two mRNA species of 3.4 kbp and 4.4 kbp were detected with the CAP-3 reactive center antisense probe. Both mRNA species encoding the CAP-3 reactive center were detected at the highest levels in placenta and lung and to a much lesser degree in all tissues examined. In addition, two minor mRNA species of approximately 7.5–8.0 kbp were also detected in these tissues. The hybridization of the Northern blots was of sufficient stringency to preclude hybridization of inexact nucleotide matches.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

I claim:

1. An isolated mammalian CAP-2 protein wherein said protein has the amino acid sequence depicted in Seq. ID No. 2 and inhibits serine protease activity or a biologically active homolog thereof.

2. The CAP-2 protein of claim 1, wherein said protein is human.

3. The CAP-2 protein of claim 1, wherein said protein comprises the amino acid sequence depicted in Seq. ID No. 2 or an allelic variant thereof.

* * * * *